United States Patent [19]

Knutson

[11] Patent Number: 4,888,414

[45] Date of Patent: Dec. 19, 1989

[54] INSULIN-BINDING PEPTIDES AND USES THEREOF

[75] Inventor: Victoria P. Knutson, Pearland, Tex.

[73] Assignee: Board of Regents, University of Texas System, Austin, Tex.

[21] Appl. No.: 36,215

[22] Filed: Apr. 9, 1987

[51] Int. Cl.$^4$ .......................... C07K 7/40; C07K 7/06; A61K 35/39

[52] U.S. Cl. .................................. 530/303; 530/328; 530/329; 530/350; 530/351; 424/110

[58] Field of Search ............... 530/303, 329, 328, 350, 530/351; 424/110

[56] References Cited

U.S. PATENT DOCUMENTS

| | | | |
|---|---|---|---|
| 3,907,765 | 9/1975 | Wang | 530/303 |
| 4,569,791 | 2/1986 | Frank et al. | 530/303 |
| 4,569,792 | 2/1986 | Frank et al. | 530/303 |
| 4,581,165 | 4/1986 | Frank et al. | 530/303 |

OTHER PUBLICATIONS

Rodionychev et al, "Delayed Hypoglycemic Activity of a Hexapeptide Analog Fragment 22-26 of Insulin B-Chain", Chemical Abstracts, vol. 93, p. 108, (161669k) 1980.

You-Min et al, "Studies on the Mechanism of Insulin Action Vi, The Interaction of Insulin Fragments with Insulin Receptor". Chemical Abstracts, vol. 93, p. 100 (161597k), 1980.

Kikuchi et al, "Studies on the Biological Activity of Degraded Insulins and Insulin Fragments", Chemical Abstracts, vol. 93, p. 77 (215776p), 1980.

Frank et al, "Modulation of Hepatic Insulin Receptors by a Human Growth Hormone Fragment (hGH6-13)", Chemical Abstracts, vol. 98, p. 144 (173579x), 1983.

Kikuchi et al, "Effect of Insulin Fragments on Biological Activity of Insulin and Desoctapeptide Insulin II Enhanced Binding and Mechanism Studies", Chemical Abstracts, vol. 95, p. 107 (181341s), 1981.

Mekler, (Biofizika, VIV (4), 1969, 581-584.

Idlis (Mendeleev Chem. J., 25:431-434).

*Primary Examiner*—Margaret Moskowitz
*Assistant Examiner*—Abdel A. Mohamed
*Attorney, Agent, or Firm*—Arnold, White & Durkee

[57] ABSTRACT

The present invention concerns a novel class of peptides which specifically bind insulin. The diverse uses of these peptides relate to insulin, insulin action and the cellular receptor for insulin. The most preferred peptide of the invention is the hexapeptide-NH$_2$-cys-val-glu-glu-ala-ser-COOH which has marked affinity for the insulin B-chain.

Antibodies having specific binding affinity for peptides of the invention have identified and forseen uses. Such antibodies specifically directed toward a preferred peptide of the invention comprising cys-val-glu-glu-ala-ser represent a further preferred aspect of antibody-related aspects of the present invention.

In one significant aspect, the present invention involves a method for determining insulin levels in a biological fluid. A further aspect of the present invention involves a process for measuring insulin receptor sites involving the binding of antibodies to cells or cell fractions.

The present invention further comprises a method for decreasing the amount of biologically active insulin present in a biological fluid such as the blood of an animal. This method involves parenterally administering an amount of peptide of the invention in free or carrier-conjugated form.

2 Claims, 8 Drawing Sheets

INSULIN-BINDING PEPTIDES AND USES THEREOF

BACKGROUND OF THE INVENTION

The present invention relates to a unique class of polypeptides which are potential antagonists for insulin in that they possess binding affinity for insulin and share apparent commonality of structure with the cellular insulin receptor binding site. In addition, the invention is directed to antibodies raised against these novel peptides which have potential diagnostic and therapeutic utility in determining the levels of insulin receptor expression and in agonizing or antagonizing the hormonal effects of insulin, respectively.

Hyperinsulinemia is a condition relating to overproduction of insulin by, for example, hyperplastic or neoplastic pancreatic B cells. This condition may also result from the parenteral overdosage of insulin to a diabetic patient. In any case, hyperinsulinemia may result in diverse and unwanted physiological effects such as disturbance of carbohydrate metabolism possibly resulting in convulsions and coma. While treatments exist for the elevation of acutely low glucose levels resulting from hyperinsulinemia, the present invention includes a method for the rapid deactivation of circulating blood insulin.

The maintenance of an appropriate insulin level is an important aim in the control of diabetics melitis. While methods for the monitoring of circulating insulin levels are available, they tend to be cumbersome and overly expensive. One advantage of the present invention is that it comprises a relatively simple, sensitive and accurate method for monitoring blood insulin levels.

An improved probe specific for the cellular insulin receptor is also inherently an advantage resulting from application of the present invention. Antibodies directed toward the polypeptides of the present invention may be used to locate, quantitate, separate or isolate cellular insulin receptor or insulin-binding components thereof.

While exact binding site for insulin on the insulin receptor is unknown, insulin has been described as having a receptor-binding domain which includes amino acid residues 22-27 of the insulin B-chain (Blundell et al. Nature, Vol. 257, pp. 197-203, Sept. 18, 1975) These residues are invariant in most mammalian insulin molecules. The nucleic acid sequence coding for human and other mammalian insulins has been reported (Bell et al., Nature, Vol. 295, pp 31-35, Jan. 7, 1982).

SUMMARY OF THE INVENTION

The present invention concerns a novel class of peptides of the formula I:

Y-Cys(Gly, Ser, Arg,, Trp)-Val(Ile, Leu, Met)-Glu(Lys)-Glu(Lys)-Ala(Pro, Ser, Thr)-Ser(Ala, Thr, Pro)-X (I)

wherein each amino acid in parentheses may be independently independently substituted for the immediate previous amino acid residue and wherein each of X and Y is independently selected from a terminal amino group, a terminal carboxy group or a non-interfering, immunologically neutral amino acid fragment of up to 10 amino acids in length.

Preferred subclasses of the peptides in accordance with the invention include peptides of formula IA:

Y-Cys(Gly, Ser, Arg)-Val(Ile)-Glu(Lys)-Glu-(Lys)-Ala(Thr, Ser, Pro)-Ser(Ala, Thr, Pro)-X (IA);

and of formula IB:

Y-Cys(Trp)-Ile(Met)-Lys-Lys-Pro-Ala (Ser)-X (IB);

wherein X, Y and the parenthetically enclosed expressions have the meaning given above. In the above preferred subclasses special preference is given to peptides wherein X is a terminal carboxyl group and Y is a terminal amino group with a peptide in accordance with formula IA having the structure $NH_2$-Cys-Val-Glu-Glu-Ala-Ser-COOH being most preferred. These peptides have a variety of diverse uses which involve chemical and biological interaction with insulin, insulin action and the cellular receptor for insulin.

Antibodies raised against and having specific binding affinity for the peptides according to the present invention have identified and forseen uses and, is such, comprise a further preferred aspect of the present invention. One preferred antibody specificity is found when an antibody is specifically directed toward an epitope located on the preferred cys-val-glu-glu-ala-ser amino acid sequence given above. A peptide comprising the cys-val-glu-glu-ala-ser amino acid sequence exhibits specific binding affinity for insulin B chain. The arg-gly-phe-phe-tyr-thr amino acid sequence of insulin B chain may represent a site of interaction for this binding. Antibodies raised against apparent epitopes of the cys-val-glu-glu-ala-ser amino acid sequence exhibit a marked affinity for a portion of the insulin receptor which may be involved with binding to the arg-gly-phe-phe-tyr-thr amino acid sequence of insulin B-chain. The arg-gly-phe-phe-tyr-thr amino acid sequence is the sequence at amino acid positions 22-27 of the insulin B-chain and is thought to represent at least part of the domain involved in the binding of insulin to the insulin receptor of cellular surfaces.

In one significant aspect, the present invention involves a method for determining insulin levels in a biological fluid. In one embodiment the method comprises first immobilizing a peptide of the present invention to a surface to produce a coated surface The most preferred peptide to be so immobilized is one comprising cys-val-glu-glu-ala-ser. The surface is preferably a plastic surface such as the polystyrene or polyvinyl chloride of a microtiter plate well. Next, a portion of the coated surface is incubated simultaneously with a trace amount of labeled insulin and a sample of biological fluid being tested for insulin content. The labeled insulin may comprise any of the labels well-known to those skilled in the pertinent arts, such as a radioisotope, a fluorescent or chromophoric compound, an enzyme or biotin. The labeled insulin will compete with insulin in the biological fluid for insulin binding sites on the coated surface, such that the insulin level in the biological fluid is measured from the extent of induced decrease in labeled insulin binding to the coated surface. Solutions of purified insulin may be used as standards in place of the biological fluid. Peptides of the present invention such as the preferable cys-val-glu-glu-ala-ser polypeptide may be used to produce the coated surface.

A further aspect of the present invention involves a process for measuring insulin receptor sites. This process initially includes the step of obtaining a peptide in 
accordance with the present invention, preferably cys-val-glu-glu-ala-ser. Such a peptide may be chemically or biologically synthesized, possibly derived from a natural or artificial polypeptide or obtained from a commercial source.

The next step of the process involves eliciting the production of antibodies directed toward the obtained peptide. The peptide again preferably comprises a cys-val-glu-glu-ala-ser amino acid sequence and the antibody is preferably directed toward an epitope of this sequence. Such elicitation may generally be conducted, for example, by subdermal administration to a mammal of the peptide, preferably conjugated to a proteinaceous carrier. The final antibody may be that derived from the mammal's serum (polyclonal) or that derived from a hybridoma resulting from fusion of antibody-producing cells of the mammal with a myeloma cell line. At this point said antibodies are preferably separated for use, for example by purification of polyclonal antibodies from serum or separation of monoclonal antibodies from tissue culture medium. In many cases, particularly when the peptide such as cys val-glu-glu-ala-ser is small (e.g., having a molecular weight of about 1,000 or less), the polypeptide may be a hapten and eliciting the production of antibodies should comprise coupling the hapten to a proteinaceous carrier to form a hapten-protein conjugate which is subdermally administered to the mammal.

Finally, the binding of the antibodies to cells or cell fractions is determined as a measure of insulin receptor sites. This binding may be measured by any of numerous methods known to those skilled in the immunologically-related arts. These methods may include usage of labeled antibodies directed, for example, toward a cys-val-glu-glu-ala-ser-containing peptide or of secondary labeled antibodies directed toward epitopes of the antibodies directed toward the cys-val-glu-glu-ala-ser.

The present invention further comprises a method for decreasing the amount of biologically active insulin present in a biological fluid such as the blood of an animal. This method may comprise the administering of a peptide according to the present invention to the animal so that the peptide appears in the biological fluid at a desired level, for example, comparable to the level of insulin present. Such desired levels (generally less than normal insulin levels on a molar basis) will serve to bind to insulin and biologically inhibit the normal insulin activity and result, for example, in the alleviation of shock induced by abnormally elevated insulin levels.

Potential uses of the insulin-binding peptides of the present invention include the measurement of insulin levels. A solid phase assay may be readily developed in which such a peptide is immobilized. Radiolabeled insulin then will compete with unlabeled insulin or serum insulin for binding to the peptide. A test kit of this type would be easier to produce than currently available radioimmunoassays for insulin. In addition, the peptide test would be less expensive to prepare and have an indefinite shelf life, as compared to currently available test systems.

A test kit may be readily developed which would allow diabetics, for example, to determine their blood insulin level at home. One type of design of such a kit would require that the insulin-binding peptide be immobilized on a matrix such as agarose beads. Insulin, which is coupled to a dye such as phenyl red, would be mixed with a drop of blood to be tested, and added to the peptide-agarose beads. At low blood insulin levels, sedimented agarose beads would have a red color. As the blood concentration of insulin rises, the agarose would gradually change in color from red to pink to white. A calibrated color chart would be included in the home kit.

Kits useful in the present invention include those of the general type described by Szczesniak, U.S. Pat. No. 3,899,298. Such kits comprise a carrier being compartmentalized to receive at least one, or at least two or at least three or more containers and to maintain said containers in closed confinement. A first container may contain an insulin-binding peptide of the present invention bound to a solid matrix such as agarose beads or to the inside surface of the container, if, for example, such container is a test tube. A second container may then contain a labeled insulin preparation. A third container may contain an unlabeled insulin standard such as an insulin solution. At a time of testing for insulin in a biological sample such as blood or serum, the labeled insulin alone and in combination with either an amount of biological sample or an amount of insulin standard may be added to the immobilize insulin-binding peptide of the first container.

The insulin in the second container may be detectably labeled as, for example, by a radiolabel or an enzyme label. Any number of variations or permutations consistent with the various techniques for use in the detection of insulin through the use of insulin-binding peptides of the present invention may be envisioned for the preparation of a kit. These are all matters of choice, determined by the ease of handling, rapidity and efficiency of the testing.

Quantitative analysis of insulin levels can be carried out by interpolation into standard binding curves, as is known in the art. A multiplicity of container means, each one having a different amount of unlabeled insulin, for example, can be present in the kit for such a purpose.

In one particular embodiment, the insulin-binding peptide may be immobilized onto plastic strips which are then brought into contact with the samples to be asaayed for insulin levels. The strip may subsequently be contacted with a solution containing an enzyme labeled anti-insulin antibody; this resulting in a "sandwich" forming on the strip. Finally, introduction of the strip into a color developing solution (such as substrate for the enzyme) and detection of color, is a rapid efficient and inexpensive method for qualitatively, and even roughly quantitatively determining insulin levels in animal samples.

As a therapeutic agent, a peptide of the present invention may be administered to a patient with a u dangerously high blood insulin level. The peptide would interact with blood insulin and biologically deactivate it by possibly binding to the region of the insulin molecule which has affinity for the insulin receptor site. This deactivation would allow for rapid clearance and elimination of the insulin-insulin-binding peptide from the body.

Antibodies generated against insulin-binding peptides react with the bona fide insulin receptor. In a clinical setting, such antibodies may be used to determine the number of insulin receptor molecules, for example, on blood cells. A correlation has been reported between low numbers of blood cell insulin receptors, and the predisposition toward adult-onset diabetes. Thus, a predisposition toward adult-onset diabetes-.may be detected by use of such antibodies.

Oligonucleotides relating to the insulin-binding peptides of the present invention and the receptor-binding portion of insulin may become useful in probing the genome for insulin receptor sequences. In this regard, useful probes in accordance with the present invention include the oligonucleotides shown in Table 1.

TABLE 1

| Insulin B-chain (22-27): —Arg—Gly—Phe—Phe—Tyr—Thr— |
|---|
| cDNA: —CGA—GGC—TTC—TTC—TAC—ACA—(5'—3') |
| cDNA: —ACA—CAT—CTT—CTT—CGG—AGC—(3'—5') |
| mRNA: —UGU—GUA—GAA—GAA—GCC—UCG—(5'—3') |

The present invention generally involves three areas relating to insulin-binding peptides of the present invention: (1) their binding to insulin or insulin derivatives, (2) the generation and use of antibodies to these peptides, and (3) the characterization of these antibodies with respect to their interaction with insulin binding peptides of the invention and purified insulin receptor.

Insulin-binding peptides may be immobilized in receptacles such as those of microtitre plates. The surface of the receptacles may be blocked against non-specific binding and then washed. A labeled insulin such as $^{125}$I-insulin may then be added to each receptacle and binding allowed to proceed. The receptacles may then be washed to remove unbound labeled insulin, and then assayed to determine the amount of bound labeled insulin. Nonspecific binding may be determined by a procedure such as incubating immobilized insulin-binding peptide with labeled insulin in the presence of an excess of unlabeled insulin.

The affinity of insulin for insulin-binding peptides may be determined by manipulations such as incubating various concentrations of labeled insulin with immobilized insulin-binding peptides (in the absence or presence of excess unlabeled insulin), and analyzing the data by the method of Scatchard.

The specificity of interaction between the insulin-binding peptides of the present invention with insulin may be found, for example, by incubation of immobilized insulin-binding peptides with material such as radio-labeled non-insulin hormones or peptides both in the presence and absence of excess unlabeled material. Additionally, specificity for human insulin may be investigated by incubating the immobilized insulin-binding peptides with a single concentration of labeled insulin and various concentrations of, for example, unlabeled porcine insulin, guinea pig insulin or desoctapeptide insulin. These insulins are listed in decreasing order of affinity for the "classical" insulin receptor of adipocytes, and should compete to varying degrees with labeled insulin for binding to immobilized insulin-binding peptides as the insulin-binding peptides reflect insulin receptor affinity for insulin. Specificity of insulin binding to insulin-binding peptides may also be tested through the use of peptides with the same empirical composition as an insulin-binding peptide but with a different sequence. This control "scrambled" peptide may be immobilized and subjected to the procedures described above.

Quantitation of the amount of an insulin-binding peptide immobilized in a receptacle may be performed, for example, with [$^3$H] or [$^{14}$C]-labeled insulin-binding peptide. The stoichiometry of insulin-binding peptide interaction with insulin may then be quantitated from the amount of immobilized insulin-binding peptide and the amount of insulin bound per well.

The immobilization of an insulin-binding peptide and a corresponding loss of degrees of configurational freedom of the immobilized peptide may substantially modify the ability of this insulin-binding peptide to interact with insulin. Only a fraction of the bound peptide may be competent to bind insulin. The solution phase interactions of an insulin-binding peptide and insulin may be determined by incubating a single concentration of unlabeled insulin with varying concentrations of labeled insulin-binding peptide. After attaining equilibrium (the time required to attain equilibrium in the solution phase may also vary from the solid phase equilibration time), free insulin-binding peptides may be separated from insulin-binding peptides bound to insulin by, for example, trichloroacetic acid-induced precipitation. A small molecule such as a free insulin-binding peptide should remain dissolved, but this may be experimentally confirmed with individual radiolabeled insulin-binding peptides. From this binding isotherm the solution phase affinity and stoichiometry for each case may be determined.

The most preferred insulin-binding peptide, IBP (cys-val-glu-glu-ala-ser), was believed to bind to a hexameric amino acid sequence of the insulin B-chain. In view of this domain of binding affinity, it is expected that free B-chain but not free A-chain may interact with IBP. The ability of intact insulin to compete with insulin B-chain or insulin A-chain for binding to an insulin-binding peptide such as IBP may be determined by adding a series of concentrations of unlabeled insulin to a single concentration of labeled A-chain or labeled B-chain in the presence of immobilized IBP. After attaining equilibrium, the wells would be washed and measured for label, for example, as described above.

The role of cysteine in the interaction of an insulin-binding peptide such as IBP and insulin may be particularly interesting because the cysteine sulfhydryl group is particularly chemically reactive. To ascertain the role of a cysteine residue of an insulin-binding peptide in the interaction with insulin, several approaches may be pursued. In one approach, the sulfhydryl group of cysteine may be oxidized by performic acid to generate cysteine sulfinic acid. In a second approach, a dimer of IBP may be synthesized, with a disulfide bond linking the two monomers. Both of these compounds may then be subjected to the binding experiments with insulin or insulin fragments, for example, as outlined above.

To generate an antigen comprising an insulin-binding peptide, the insulin-binding peptide may be conjugated with a cross-linking agent to a proteinaceous carrier such as welk hemocyanin. Animals subdermally administered such a conjugate, in a manner calculated to optimize antibody production, produce usable amounts of antibody having binding affinity for the insulin-binding peptide. Preliminary characterization of such antibody may be performed by assessing its ability to interact with the insulin-binding peptide which it was produced against.

The insulin-binding peptide may, for example, be blotted onto a nitrocellulose membrane. After blotting the peptide, the nitrocellulose membrane would be dried. The dried membrane should then blocked with, for example, gelatin to minimize non-specific binding. Dilutions of the immune and pre-immune (control) antibodies may be used. Replicate aliquots of immune and pre-immune antibody may be added to microtiter receptacle wells. The nitrocellulose membrane should then be positioned over the receptacle wells so as to align the blotted insulin-binding peptides and the wells. A thin gasket may then be placed on top of the membrane, and the whole assembly sandwiched between plastic plates and clamped together. The sandwich should then be inverted, and antibody allowed to incubate with immobilized insulin-binding peptide. Following incubation, the sandwich should be inverted to allow the antibody to flow back into the wells. The nitrocellulose membrane preferably is then washed with buffers containing high salt and detergent. The membrane may then be incubated with $^{125}$I-labeled Protein A. Following additional washings, the membrane should be blotted dry and subjected to autoradiography. Alternatively, individual spots on the membrane can be cut out and assayed for label directly. By immobilizing insulinbinding peptides on the nitrocellulose and incubating with dilutions of serum, the titre of antibody can be determined. Crude detergent extracts of cellular membranes or purified insulin receptor may be immobilized on the nitrocellulose and incubated with dilutions of antibody. The affinity of antibody for cells or purified receptor may be assessed by this or other means. All antibody assays should be run with control IgG from, for example, pre-immune or hemocyanin-injected rabbits.

The specificity of the antibody for the insulin receptor may be determined,for example, by metabolically labeling cultured adipocyte cells with $^{75}$Se-methionine. The membrane proteins of the labeled cells may be extracted with detergent, and the antibody incubated with the detergent extract. The complex may be extracted from solution with Protein A-agarose, and boiled with SDS-polyacrylamide gel sample buffer. The soluble materials resulting from this treatment may then be subjected to polyacrylamide gel electrophoresis. Following staining, distaining and drying of the gel, it should be subjected to autoradiography. The autoradiogram should demonstrate a 135 kDa and a 93 kDa band, under reducing conditions for antibody specifically reacting with the insulin receptor. Tq demonstrate the submit specificity; of the antibody, crude cell extracts or purified receptor may be subjected to SDS-PAGE. The protein bands on the gel should then be blotted onto nitrocellulose, and the nitrocellulose incubated with antibody. Following washing of the membrane, the nitrocellulose should be incubated with $^{125}$I-Protein A, as described above. Autoradiography of the membranes should demonstrate a band at 135 kDa if the antibody is interacting with the insulin binding subunit of the insulin receptor.

The ability of an antibody against an insulin-binding peptide to inhibit the binding of insulin to the insulin receptor may be measured, for example, with intact cell monolayers of adipocytes. Various dilutions of antibody and labeled insulin should be added to the cell monolayers in the presence and absence of an unlabeled insulin excess. The cells incubated in the presence of unlabeled insulin may be used to assess the level of non-specific insulin binding. After incubating, the cell monolayer should be washed to remove unbound insulin, the monolayers solubilized and the label quantitated to determine the level of specifically bound insulin. If insulin binding is inhibited by antibody, further characterization of this interaction may be performed by, for example, generating Scatchard plots in the presence or absence of a single dilution of the antibody. These manipulations should allow the determination of whether the antibody is modifying the affinity of insulin itself for the receptor, or masking insulin binding sites on the receptor.

The ability of an antibody against insulin-binding peptide to inhibit insulin action may be probed, for example, by determining the ability of the antibody to modify the uptake of the glucose analog, 2-deoxyglucose. For example, intact monolayers of cultured mammalian cells may be washed with a glucose-free buffer, and the cells incubated in the presence or absence of antibody. Following an additional incubation in the presence or absence of insulin, an aliquot of [$^3$H]-2-deoxyglucose may be added to the monolayers. The uptake of radiolabel may be stopped, for example, by rapid washing of the monolayers with cold buffer containing 15 mM glucose. If the antibody acts as an insulin antagonist, it should inhibit the insulin-stimulated uptake of deoxyglucose. If the antibody acts as an insulin agonist, the presence of antibody alone should augment the uptake of deoxyglucose.

The following examples are presented to describe preferred embodiments and utilities of the present invention and are not meant to limit the present invention unless otherwise specifically stated in the claims appended hereto.

EXAMPLE 1

The Binding Of IBP To Insulin

Insulin Binding Peptide, synthesized by OCS Laboratories, Inc., Denton, Tex., was immobilized in the wells of flexible, U-bottom 96-well polyvinyl chloride microtitre plates (Falcon, Becton Dickinson Labware). To each well was added 100 ul of the peptide (5 ug/ml in 0.1 M sodium carbonate, pH 9.6). The peptide was allowed to adsorb to the well overnight at 4° C. Unreacted sites in the wells were blocked with 150 ul of 1% ovalbumin (Sigma Chemical Co.) in 0.1M sodium carbonate, pH 9.6, for 1 h at room temperature. The wells were washed two times with phosphate-buffered saline (PBS) containing 0.1% BSA (Fraction V, Sigma Chemical Co.), and then incubated with $^{125}$I-insulin in PBS, 0.1% BSA, for 3 h at room temperature. The wells were then washed 3 times with PBS-0.1% BSA, and were then excised from the plate and counted in a gamma counter. Total binding of insulin to the IBP was determined with iodinated insulin alone. Nonspecific binding was determined in the presence of radiolabeled insulin plus 3 uM unlabeled insulin. Specific binding was calculated as the difference between total and nonspecific binding. All values are reported as specific binding, unless otherwise indicated. All determinations (both total and nonspecific) were performed in triplicate. Insulin was iodinated by the method of Chloramine T, as previously described (Gavin et al., *Proc. Nat. Acad. Sci.*, Vol. 71, p. 84–88 (1974)).

Figure 1:
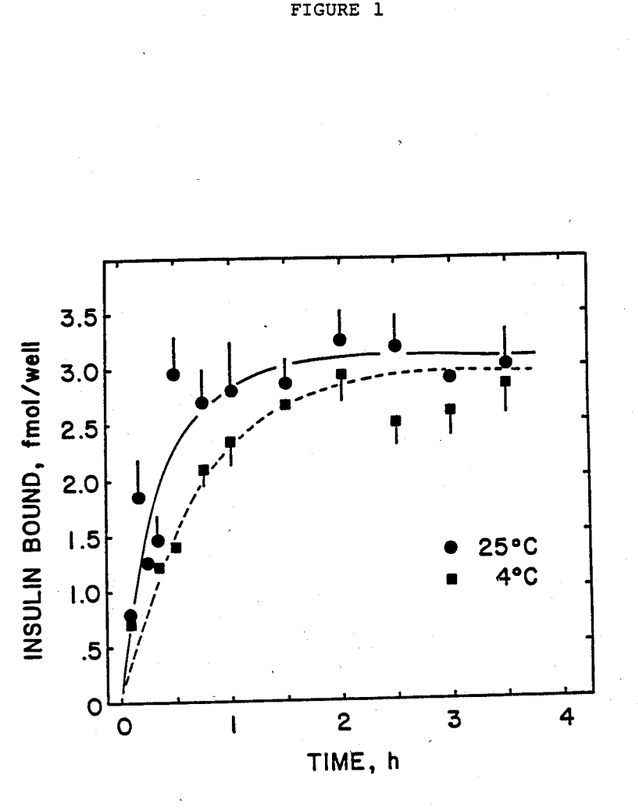

FIG. 1 shows the time- and temperature-dependence of insulin binding to IBP. The peptide was immobilized in the bottom of 96-well microtitre plates, and at zero time, 2 nM $^{125}$I-insulin, in the absence or presence of 3 uM unlabeled insulin, was added to each of the wells. At the indicated times, the wells were washed with cold PBS, the washed wells were cut from the dish and counted for radioactivity. The indicated data points are average values of specifically bound insulin, and the error bars indicate the range of the data. At 25° C., the binding attained equilibrium within 1.5 h, with a half-time of approximately 20 min. At 4° C., the binding process is slightly slower, requiring approximately 2 h to attain an equilibrium level of binding.

Figure 2:
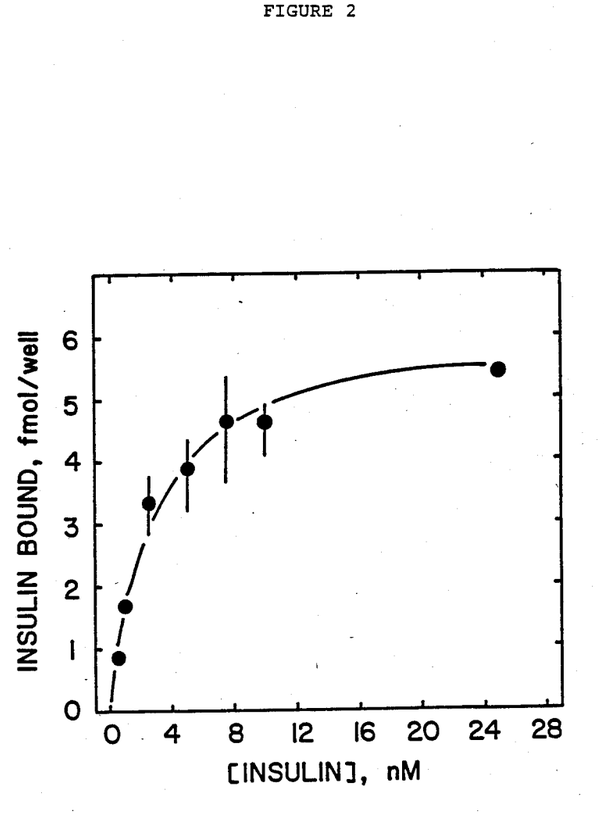
Figure 3:
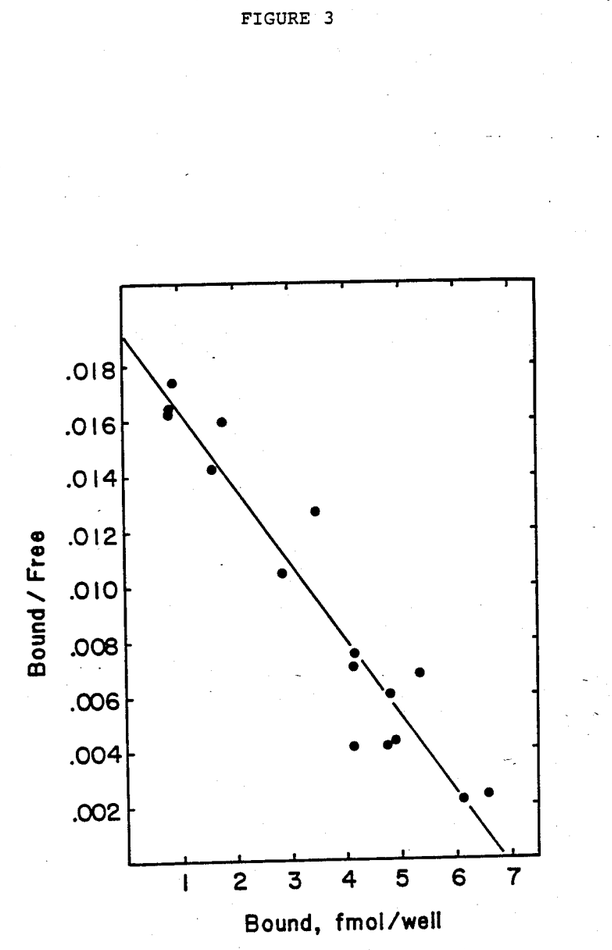

FIG. 2 shows the concentration-dependence of insulin binding to IBP. The peptide was immobilized in the bottom of 96-well microtitre plates, and $^{125}$I-insulin, in the absence or presence of 3 uM unlabeled insulin, was added to the wells. Following incubation at 25° C. for 3 h, the wells were washed, cut from the dish, and counted, as described above. The indicated data points of FIG. 2 are average values of specifically bound insulin, the error bars indicate the range of the data. FIG. 3 shows a Scatchard analysis (Scatchard, *Ann. N.Y. Acad. Sci.*, Vol. 51, pp. 660–672 (1949)) of the binding data shown in FIG. 2.

As demonstrated in FIG. 2, the specific binding of insulin to IBP is a concentration-dependent, saturable process. Plotting of the binding isotherm data according to the method of Scatchard, as in FIG. 3, demonstrates a linear plot, with a $K_d$ of 3 nM.

EXAMPLE 2

SPECIFICITY OF IBP BINDING

The specificity of the binding of IBP to insulin was determined by incubating iodinated calcitonin, parathyroid hormone or atrial naturiuretic peptide with immobilized IBP. The binding of insulin to IBP appears to be a specific process. The specific binding of the low molecular weight polypeptide hormones calcitonin, parathyroid hormone and atrial naturiuretic peptide is less than 1% of the level of the specific binding of insulin (Ins) to IBP.

Figure 4:
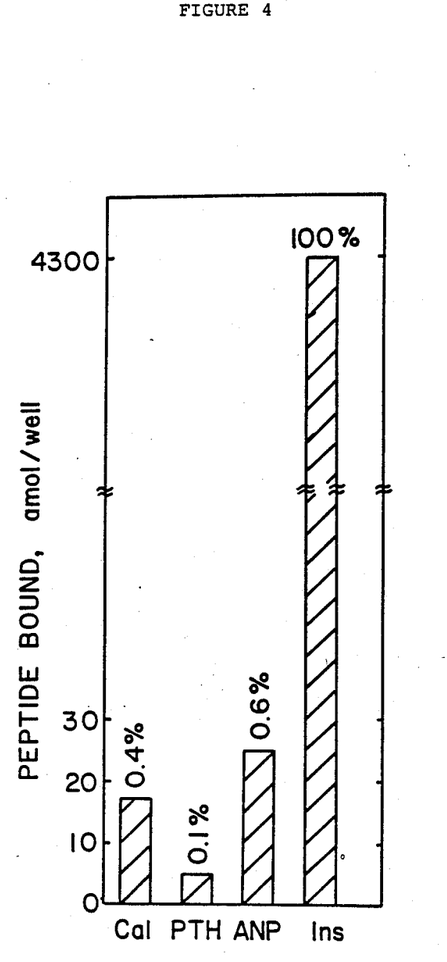

The binding of immobilized IBP to various polypeptide hormones is shown in FIG. 4. The insulin-binding peptide was immobilized in the bottom of 96-well microtitre plates. To the wells were then added 2 nM iodinated polypeptide hormones in the absence or presence of at least a 1000-fold excess of unlabeled hormone. Following incubation at room temperature for 3 h, the wells were washed, excised from the plate and $^{125}$I measured as described above. The specific binding of hormone to the wells is indicated, along with the binding as a percentage of the binding of insulin to the wells. The polypeptide hormones utilized are indicated on the abcissa: Cal, calcitonin; PTH, parathyroid hormone; ANP, atrial naturiuretic peptide; Ins, insulin. Thus the binding specificity of the insulin-binding peptides of the present invention was clearly demonstrated.

EXAMPLE 3

Specificity Of Insulin Binding

The binding specificity of iodinated insulin for immobilized peptides was determined. Peptides of various sequences and sizes were immobilized in microtitre wells, as described in Example 1. The peptides utilized were IBP (CVEEAS) and a series of control peptide having the following designations and amino acid sequences: S28, TTHYQKG; S79, AQGHRPQDEG; S81, YGSLPQKAQGHRPQDEG; S82, THYGSLPQKAQGHRPQDEG; and EAE, FSWGAEGQR.

Figure 5:
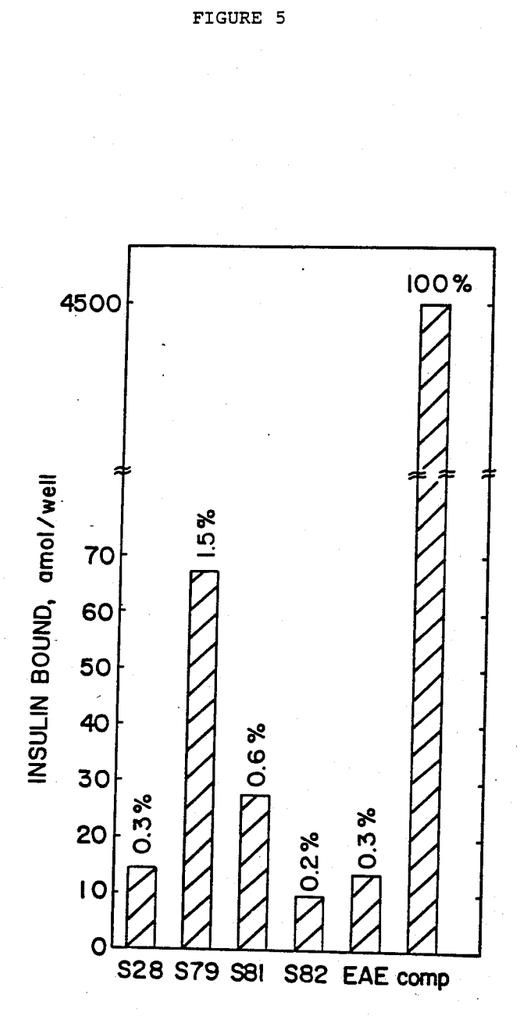

Peptides were dissolved in buffer at a concentration of 5 ug/ml, and immobilized in the wells of the microtitre plate. The immobilized peptides were then incubated with 2 nM $^{125}$I-insulin in the absence or presence of 3 uM unlabeled insulin, as described above. The specific binding of insulin to immobilized peptide is indicated, alone with the binding as a percentage of the binding of insulin to immobilized IBP. The peptides utilized are indicated on the abcissa. The binding of insulin to various immobilized peptides appears to be specific, as shown in FIG. 5. The respective relative binding of insulin (shown in FIG. 5) was IBP-100%, S28-0.3%, S79-1.5%, S81-0.6%, S82-0.2% and EAE-0.3%. Thus, the binding, specificity of insulin for IBP further demonstrated the insulin-binding characteristics of the insulin-binding peptides of the present invention.

The data presented in FIGS. 1 through 5 indicate that the binding of insulin to immobilized IBP is a high affinity, saturable, time- and temperature-dependent interaction, with a high degree of specificity.

EXAMPLE 4

Generation of Antibodies to IBP

Three mg of welk hemocyanin and 10 mg of IBP were dissolved in a total volume of 0.9 ml of PBS. After the addition of 100 ul of 0.5% glutaraldehyde, the solution was stirred overnight at room temperature. The mixture was then diluted to a total volume of 3 ml with PBS, resulting in a stock solution which was 1 mg/ml in carrier protein. The initial immunization of the rabbits was performed with complete Freund's adjuvent, containing 250 ug of immunogen (250 ul of stock), 250 ul of PBS and 500 ul of Freund's complete adjuvant. Eachrabbit was injected subdermally on the back, at 5 separate sites, 200 ul injected at each site. One month after the initial injection, each animal was boosted withincomplete adjuvant. Two weeks after the boost, the rabbits were bled from the ear vein to determine the titre of antibody against IBP. Boosting of the animals was continued at monthly intervals, bleeding the animals at 2 week intervals after each boost. Every third month, the animals were boosted with Freund's complete adjuvant. Antibodies against IBP were thus raised.

EXAMPLE 5

Characterization of Anti-IBP Antibodies

To raise antibody against the IBP, the IBP was coupled to hemocyanin and injected intjected into rabbits, as described in Example 4. The antibody generated in the rabbits was titred by incubating antiserum or preimmune serum with IBP immobilized on nitrocellulose. The antibody binding to the nitrocellulose was probed with $^{125}$I-protein A.

Initial characterization of the antiserum was performed by assessing its ability to interact with the IBP. The IBP was immobilized onto nitrocellulose (0.45 micron, BioRad) that was sandwiched in a 96 well "Biodot" vacuum apparatus (BioRad) by adding 50 ul of IBP (5 ug/ml in 0.1M sodium carbonate buffer, pH 9.6) to each well of the apparatus. The IBP was allowed to adsorb to the nitrocellulose in the absence of an externally applied vacuum for 1 h. A vacuum was then gently applied to the Biodot apparatus in order to pull the remaining liquid through the nitrocellulose. The side of the membrane to which the peptide was applied was then marked, and the membrane was air-dried overnight. Unreacted sites on the membrane were then blocked with blot buffer (50 mM Tris, 0.5M NaCl, pH 7.5) containing 3% gelatin, by incubating the membrane in 100 ml of the buffer for 1 h at room temperature with constant agitation. The membrane was then blotted dry with Whatmann 3 MM filter paper before incubation with antibody. Dilutions of antisera, preimmune antisera or normal rabbit IgG were made in blot buffer containing 1% gelatin. Replicate 100 ul aliquots of the antisera dilutions were added to the wells of polystyrene flat-bottomed 96 well microtitre plates, the nitrocellulose membrane was positioned over the microtitre plate so as to align the immobilized IBP and the wells of the plate. A thin compressible plastic gasket was placed on top of the membrane, and the whole assembly was sandwiched between glass plates and clamped together. The sandwich was inverted, and the antibody was allowed to incubate with the immobilized IBP for 2 h at room temperature. Following incubation, the sandwich was inverted to allow the antibody to flow back into the wells of the microtitre plate. The nitrocellulose membrane was then quickly washed twice with blot buffer containing 0.25% gelatin and 0.05% Tween 20. The membrane was then incubated with 15 ml of $^{125}$I-protein A (Amersham), 1.5 uCi/15 ml, in blot buffer containing 1% gelatin, for 1 h at room temperature, with constant agitation. The nitrocellulose was then quickly washed 4 times with blot buffer containing 0.25% gelatin and 0.05% Tween 20, and then washed 2 times with blot buffer alone. The membrane was then blotted dry and subjected to autoradiography or the dots were cut from the sheet of nitrocellulose and counted in a gamma counter.

Figure 6:
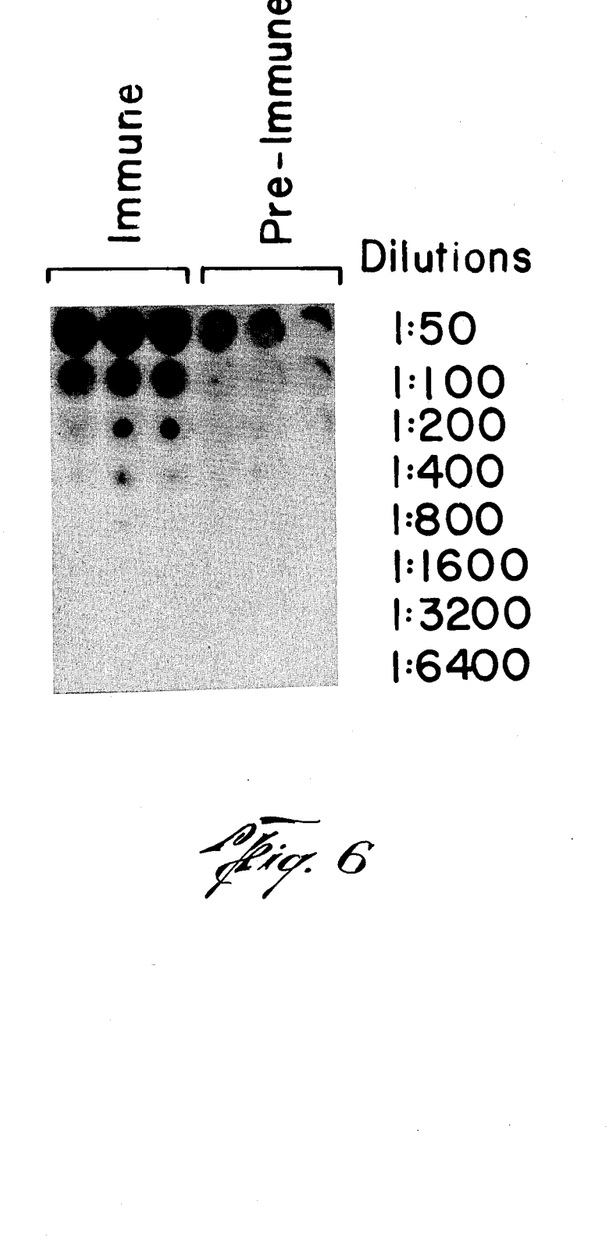

The injection of hemocyanin-coupled IBP into rabbits resulted in the generation of an antibody that reacted with immobilized IBP. As shown in FIG. 6 antisera from early bleed animals demonstrated a signal at dilutions as great as 1:400, compared to pre-immune serum. Since this "dot-blot" assay is based on the binding of the antibody to protein A, the antibody appeared to be of an IgG class.

EXAMPLE 6

Inhibition by Anti-IBP Antibody of Insulin Binding To Intact Cells

Figure 7:
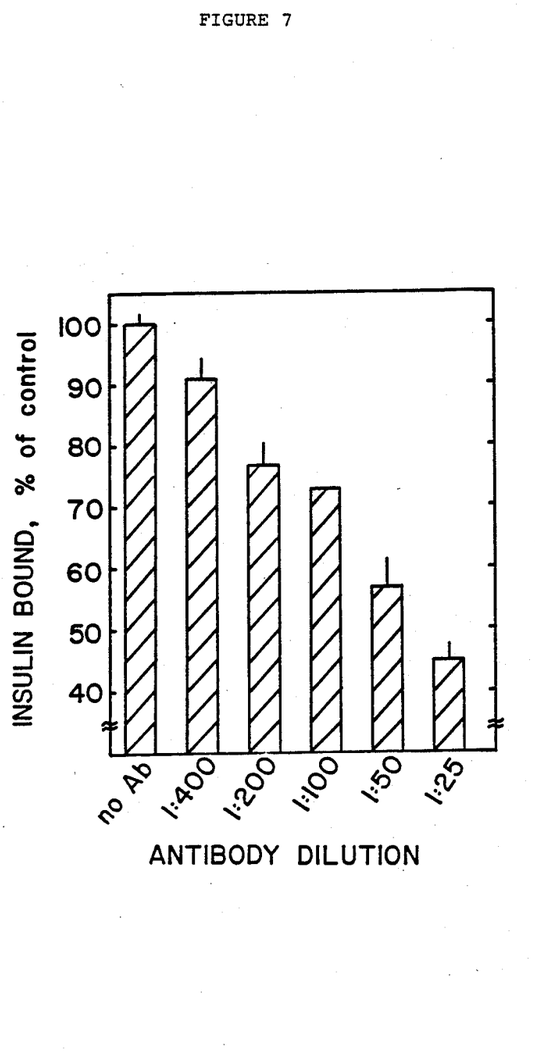

The effects of the above described antisera on insulin binding to the insulin receptor and insulin action were determined with confluent monolayers of adipocyte-like 3T3-L1 cells. These cells were seeded onto 24-well tissue culture dishes (Falcon, Becton Dickinson Labware) and induced to differentiate into adipocytes as previously described (Ronnett et al., J. Biol. Chem., Vol. 257, pp. 4285–4291 (1982)). The effect of antisera on insulin binding was determined by the co-addition of 25 mM of $^{125}$I-insulin and various dilutions of antisera to the cell monolayers in the presence or absence of an excess of unlabeled insulin. After incubation for 18 h at 4° C., the cells were washed with cold PBS to remove unbound insulin, the monolayers were solubilized in 1N NaOH, and counted to determine the level of specifically bound insulin. The effect of anti-IBP antibody on the binding of insulin to the insulin receptor in intact cell monolayers is shown in FIG. 7. The error bars indicate the range of data. Increasing concentrations of antisera resulted in increasing inhibition of specific insulin binding to cells, such that, at a 1:25 dilution of antiserum, insulin binding was inhibited by greater than 5 %. Corresponding dilutions of pre-immune serum had no effect on insulin binding to the cells.

EXAMPLE 7

Effect Of Anti-IBP Anitbody On Deoxyglucose Uptake

The ability of the antisera to IBP obtained as described in Examples 4 and 5 to modify insulin action was determined by determining its effects upon the cellular uptake of the non-metabolizable glucose analog, 2-deoxyglucose. Intact monolayers of 3T1-L1 adipocytes were washed with glucose-free Krebs-Ringer phosphate (KRP) buffer, and the cells were incubated in the presence or absence of antisera for 20 min at 37° C. Following an additional 20 min incubation in the presence or absence of insulin, an aliquot of [$^3$H]2-deoxyglucose was added to the monolayers, and the uptake of radiolabel was assessed.

Figure 8:
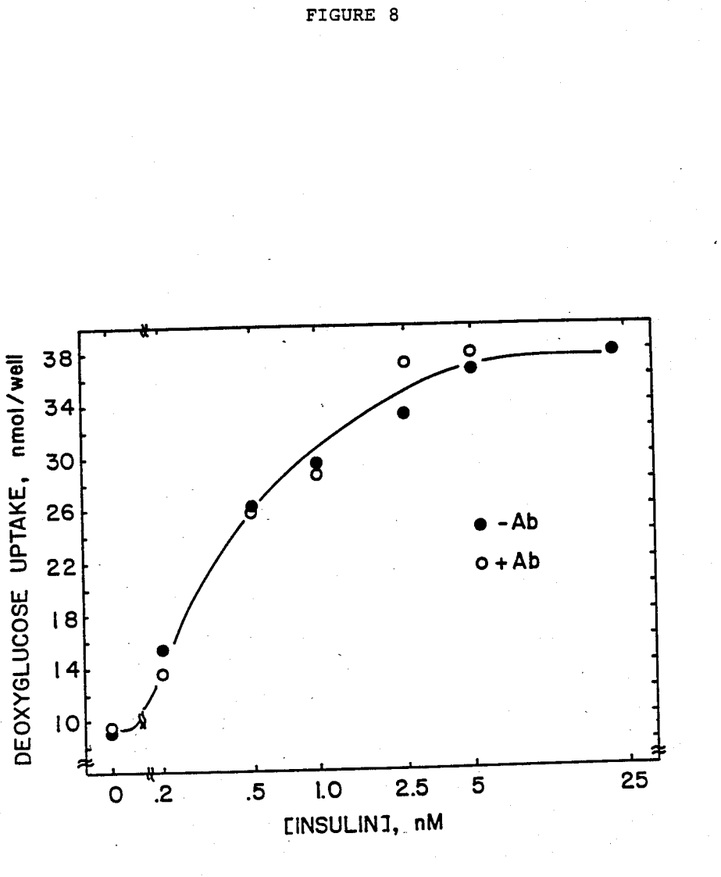

The time-dependent uptake of radiolabel was linear over this 20 min period. Uptake was terminated by the addition of ice-cold KRP buffer containing 25 mM glucose, and cell-associated radioactivity was measured. FIG. 8 shows the cellular deoxyglucose as a function of insulin concentration in the presence or absence of anti-IBP antiserum. Surprisingly, the antibody had no effect on the basal or insulin-stimulated uptake of [H$^3$]2-deoxyglucose at dilutions of antibody that inhibited insulin binding by 45% (as shown in FIG. 7). The mechanism by which insulin can be attenuated with no effect on insulin action to be definitively explained.

Changes may be made in peptides, antibodies or the steps or the sequence of the methods described herein without departing from the concept and scope of the invention as de in the following claims.

What is claimed is:

1. A peptide having the formula Y-Cys-Val-Glu-Glu-Ala-Ser-X; wherein each of X and Y is independently selected from the group consisting of a terminal amino group and a terminal carboxyl group.

2. The peptide of claim 1 wherein Y is a terminal amino group and X is a terminal carboxyl group.

* * * * *

UNITED STATES PATENT AND TRADEMARK OFFICE
CERTIFICATE OF CORRECTION

PATENT NO. : 4,888,414

DATED : December 19, 1989

INVENTOR(S) : Victoria P. Knutson

It is certified that error appears in the above-identified patent and that said Letters Patent is hereby corrected as shown below:

In column 1, line 4, insert the sentence --The United States government may have certain rights in this invention because research relating to the invention was partially supported by National Institutes of Health, Grant No. AM35397.--

Signed and Sealed this

Eighth Day of December, 1992

Attest:

DOUGLAS B. COMER

*Attesting Officer*  *Acting Commissioner of Patents and Trademarks*